United States Patent [19]
Yoon et al.

[11] Patent Number: 5,929,083
[45] Date of Patent: Jul. 27, 1999

[54] OXAZOLIDINONE DERIVATIVES AND A METHOD FOR THE PREPARATION THEREOF AND AN ANTIBACTERIAL COMPOSITION CONTAINING THE SAME

[75] Inventors: Yeo Hong Yoon; Hak Sung Kim, both of Seoul; Kwang Ho Lee, Seocho-ku; Kwang Hyuk Lee, Sungram; Jin Ah Kang, Kyungkeedo; Youn Ha Lee, Kyungkeedo, all of Rep. of Korea

[73] Assignee: Cheil Jedang Corporation, Seoul, Rep. of Korea

[21] Appl. No.: 08/891,835

[22] Filed: Jul. 14, 1997

[30] Foreign Application Priority Data

May 24, 1997 [KR] Rep. of Korea ...................... 97-20523

[51] Int. Cl.[6] ...................... A61K 31/435; C07D 221/20; C07D 221/22

[52] U.S. Cl. ............................ 514/278; 514/299; 546/16; 546/112

[58] Field of Search ...................... 546/112, 16; 514/299, 514/278

[56] References Cited

FOREIGN PATENT DOCUMENTS

96/15130  5/1996  WIPO .

*Primary Examiner*—Evelyn Mei Huang
*Attorney, Agent, or Firm*—Burns, Doane, Swecker & Mathis, L.L.P.

[57] ABSTRACT

An antibacterially effective compound of formula I:

Formula I

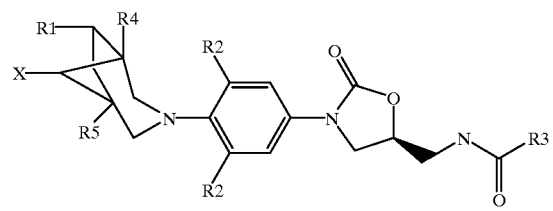

or a salt or hydrate thereof in which R1, R2, R3, R4, R5, X are as defined herein. Further, a process for producing the compound of formula I and an antibacterial composition containing antibacterially effective amount of the compound of formula I are disclosed.

28 Claims, No Drawings

OXAZOLIDINONE DERIVATIVES AND A METHOD FOR THE PREPARATION THEREOF AND AN ANTIBACTERIAL COMPOSITION CONTAINING THE SAME

FIELD OF THE INVENTION

The present invention relates to novel phenyloxazolidinone derivatives and a process for producing the same. The compounds are useful antibacterial agents, effective against a number of human and veterinary pathogens, including Gram-positive aerobic bacteria such as Staphylococcus, Streptococcus and Enterococcus as well as anaerobic microorganisms such as Clostridia sp., and acid-fast microorganisms such as Micobacterium sp., for example *Mycobacterium tuberculosis, Mycobacterium avium*. In addition, the present invention relates to an antibacterial composition containing the said phenyloxazolidinone compounds as active component.

BACKGROUND OF THE INVENTION

International Patent Publication Nos. WO 96/15130 and WO 95/25106 discloses phenyloxazolidinone derivatives having a bicyclic thiazine or oxazine phenyl substituent. Some compounds possess useful antibacterial activity against Gram-positive bacteria such as *Staphylococcus aureus* and *Streptococcus pneumonia*. However, these compounds are less antibacterially effective than well-known antibiotic vancomycin.

The present inventors conducted a long intensive investigation for the development of novel oxazolidinone compounds which have superior activity against Gram-positive bacteria to the well-known antibiotic vancomycin. Novel oxazolidinone derivatives having bicyclic substituents, which are structurally distinguished from those as disclosed in International Patent Publication Nos. WO 96/15130 and WO 95/25106 have now been developed. It was found that the present novel oxazolidinone derivatives possesses almost same or higher antibacterial activity against a variety of Gram-positive bacteria compared to the well-known antibiotic vancomycin.

SUMMARY OF THE INVENTION

In one aspect, the present invention provides a compound of the general formula I:

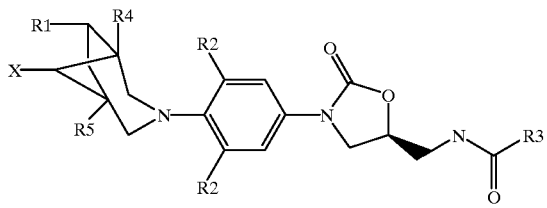

Formula I or a salt or hydrate thereof in which

R1, R4 and R5 are independently selected from the group consisting of (i) hydrogen, (ii) $C_1$–$C_6$ alkyl unsubstituted or substituted with at least one of F, Cl, hydroxy, $C_1$–$C_3$ alkyl, $C_1$–$C_6$ alkoxy and $C_1$–$C_6$ acyloxy and (iii) $C_3$–$C_6$ cycloalkyl;

R2 is independently H, F, Cl or methoxy;

R3 is selected from the group consisting of (i) hydrogen, (ii) $C_1$–$C_6$ alkyl unsubstituted or substituted with at least one of F, Cl, hydroxy, $C_1$–$C_3$ alkyl, $C_1$–$C_6$ alkoxy and $C_1$–$C_6$ acyloxy, (iii) $C_3$–$C_6$ cycloalkyl, (iv) amino, (v) $C_1$–$C_6$ alkylamino, (vi) $C_1$–$C_6$ dialkylamino and (vii) $C_1$–$C_6$ alkoxy; and X is selected from the group consisting of (i) carbonyl, (ii) thiocarbonyl, (iii) ethyleneketal, propyleneketal, dimethylketal or diethylketal, (iv) oxime unsubstituted or substituted with hydrogen, $C_1$–$C_5$ alkyl which may be in turn substitued with at least one of Cl, F, hydroxy, $C_1$–$C_3$ alkoxy and $C_1$–$C_6$ acyloxy, or $C_1$–$C_5$ acyl which may be in turn substitued with at least one of Cl, F, hydroxy, $C_1$–$C_3$ alkoxy and $C_1$–$C_6$ acyloxy, (v) hydrazone unsubstituted or substituted with hydrogen, $C_1$–$C_5$ alkyl which may be in turn substituted with at least one of Cl, F, hydroxy, $C_1$–$C_3$ alkoxy, $C_1$–$C_3$ acyloxy and phenyl, $C_1$–$C_5$ acyl which may be in turn substituted with at least one of Cl, F, hydroxy, $C_1$–$C_3$ alkoxy, $C_1$–$C_3$ acyloxy and phenyl, $C_1$–$C_5$ alkoxycarbonyl which may be in turn substituted with at least one of Cl, F, hydroxy, $C_1$–$C_3$ alkoxy, $C_1$–$C_3$ acyloxy and phenyl, or $C_1$–$C_5$ alkylsulfonyl (vi) imine unsubstituted or substituted with hydrogen, $C_1$–$C_5$ alkyl which may be in turn substituted with at least one of Cl, F, hydroxy, $C_1$–$C_3$ alkoxy, $C_1$–$C_3$ acyloxy and phenyl, or $C_1$–$C_5$ acyl which may be in turn substituted with at least one of Cl, F, hydroxy, $C_1$–$C_3$ alkoxy, $C_1$–$C_3$ acyloxy and phenyl, and (vii) carbon-carbon double bond unsubstituted or substituted with hydrogen, $C_1$–$C_4$ alkoxycarbonyl, or $C_1$–$C_4$ alkyl which may be in turn substituted with Cl, F, hydroxy, $C_1$–$C_3$ alkoxy or phenyl.

In another aspect, the present invention provides a process for producing the compound of the general formula I.

In still another aspect, the present invention provides an antibacterial composition containing antibacterially effective amount of the compound of the general formula I.

DETAILED DESCRIPTION OF THE INVENTION

The present invention relates to novel phenyloxazolidinone derivatives having bicyclic substituents. "Alkyl" herein means carbons atom chain having the designated number of carbon atoms which can be either straight chained or branched, and includes, for example, methyl, ethyl, n-propyl, n-butyl, s-butyl, t-butyl, n-pentyl, neo-pentyl.

"Acyl" includes, for example, formyl, acetyl and propionyl, and isomers thereof.

The R2 substituents may be both H or F and, preferably, one is F and another is H.

The R3 substituent is preferably hydrogen, difluoromethyl, dichloromethyl, hydroxymethyl or methoxy and, most preferably, methyl.

The preferred absolute configuration at C-5 of the oxazolidinone ring of the compounds of the present invention is (S) under the Cahn-Ingold-Prelog nomenclature system. It is the (S)-enantiomer which possesses pharmacologically superior antibacterial activity. The racemic mixture may be used as an antibacterial agent. The racemic mixture possesses about half as much antibacterial activity as the (S)-enantiomer. Therefore, it is oxazolidinone derivatives having (S)-enantiomer at C-5 of the oxazolidinone ring that constitutes a hub of the present invention.

Preferred compounds of the present invention are as follows:

(S)-N-[[3-[3-fluoro-4-(7-exo-methylspiro-[3-azabicyclo[3.1.1]heptan-6,2'-perhydro[1,3] dioxolane]-3-yl) phenyl]-2-oxo-5-oxazolidinyl]methyl]acetamide;

(S)-N-[[3-[3-fluoro-4-(7-exo-methyl-6-oxo-3-azabicyclo[3.1.1]heptan-3-yl)phenyl]-2-oxo-3-oxazolidinyl]methyl]acetamide;

(S)-N-[[3-[3-fluoro-4-(7-exo-methyl-6-hydroxyimino-3-azabicyclo[3.1.1]heptan-3-yl) phenyl]-2-oxo-5-oxazolidinyl]methyl]acetamide;

(S)-N-[[3-[3-fluoro-4-(7-exo-methyl-6-methoxyimino-3-azabicyclo[3.1.1]heptan-3-yl) phenyl]-2-oxo-5-oxazolidinyl]methyl]acetamide;

(S)-N-[[3-[3-fluoro-4-(spiro[3-azabicyclo[3.1.1]heptan-6,2'-perhydro[1,3]dioxolane]-3-yl) phenyl]-2-oxo-5-oxazolidinyl]methyl]acetamide;

(S)-N-[[3-[3-fluoro-4-(6-oxo-3-azabicyclo[3.1.1]heptan-3-yl)phenyl]-2-oxo-5-oxazolidinyl] methyl]acetamide;

(S)-N-[[3-[3-fluoro-4-(6-hydroxyimino-3-azabicyclo[3.1.1]heptan-3-yl)phenyl]-2-oxo-5-oxazolidinyl]methyl]acetamide;

(S)-N-[[3-[3-fluoro-4-(6-methoxyimino-3-azabicyclo[3.1.1]heptan-3-yl)phenyl]-2-oxo-5-oxazolidinyl]methyl]acetamide;

(S)-N-[[3-[3-fluoro-4-(1-methyl-spiro[3-azabicyclo[3.1.1]heptan-6,2'-perhydro[1,3]dioxolane]-3-yl)phenyl]-2-oxo-5-oxazolidinyl]methyl]acetamide;

(S)-N-[[3-[3-fluoro-4-(1-methyl-6-oxo-3-azabicyclo[3.1.1]heptan-3-yl)phenyl]-2-oxo-5-oxazolidinyl]methyl]acetamide;

(S)-N-[[3-[3-fluoro-4-(1-methyl-6-hydroxyimino-3-azabicyclo[3.1.1]heptan-3-yl)phenyl]-2-oxo-5-oxazolidinyl]methyl]acetamide; and (S)-N-[[3-[3-fluoro-4-(1-methyl-6-methoxyimino-3-azabicyclo[3.1.1]heptan-3-yl)phenyl]-2-oxo-5-oxazolidinyl]methyl]acetamide.

The oxazolidinone derivatives of the present invention can be combined with organic or inorganic acids to form pharmaceutically acceptable nontoxic salts. Acid addition salts include sulfate, nitrate, phosphate, hydrochloride, hydrobromide, acetate, lactate, tartrate, pamoate, succinate, ethanedisulfonate, sulfamate, benzoate, etc.

The process for producing the compound of the general formula I according to the present invention comprises the following steps:

(a) reacting a compound of the general formula XVII:

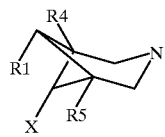

Formula XVII in which R1, R4, R5 and X represent the same as defined above, with a compound of the general formula II:

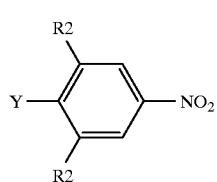

Formula II in which R2 represents the same as defined above and Y is halogen or trifluoromethane sulfonate, to provide a compound of the general formula III:

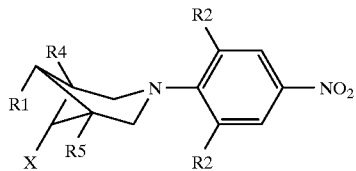

Formula III in which R1, R2, R4, R5 and X represent the same as defined above;

(b) reducing the compound of the general formula III to provide a compound of the general formula IV:

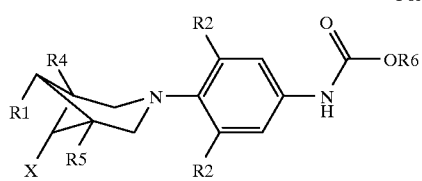

Formula IV in which R1, R2, R4, R5, X represent the same as defined above and R6 is methyl or benzyl;

(c) reacting the compound of the general formula IV with (R)-(-)-glycidyl butyrate to provide a compound of the general formula V:

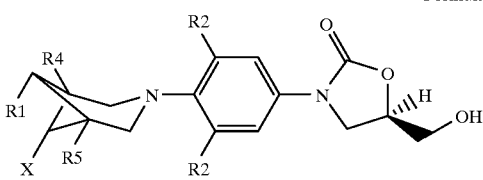

Formula V in which R1, R2, R4, R5 and X represent the same as defined above;

(d) inducing mesylation or tosylation of the compound of the general formula V to provide a compound of the general formula VII:

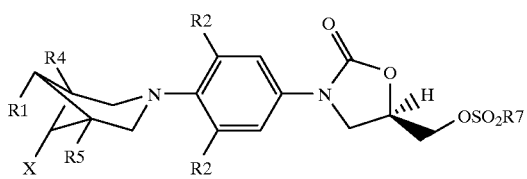

Formula VII in which R1, R2, R4, R5 and X represent the same as defined above and R7 is methyl or 4-methylphenyl;

(e) inducing amination of the compound of the general formula VII, followed by acylation to yield the compound of the general formula I.

The optically pure enantiomer of the oxazolidinone derivatives according to the present invention can be synthesized in reference to J. Med. Chem., 39, (1996), p 9673 and J. Med. Chem., 35, (1992), p 1156. The whole procedure for the synthesis of the oxazolidinone of the general formula I according to the present invention is depicted in Reaction Schemes I and II. The starting 3-aza-[3.1.1]-heptane heterocyclic amine derivatives (XVII) can be synthesized in reference to Heterocycle, 25.,(1989), p 29.
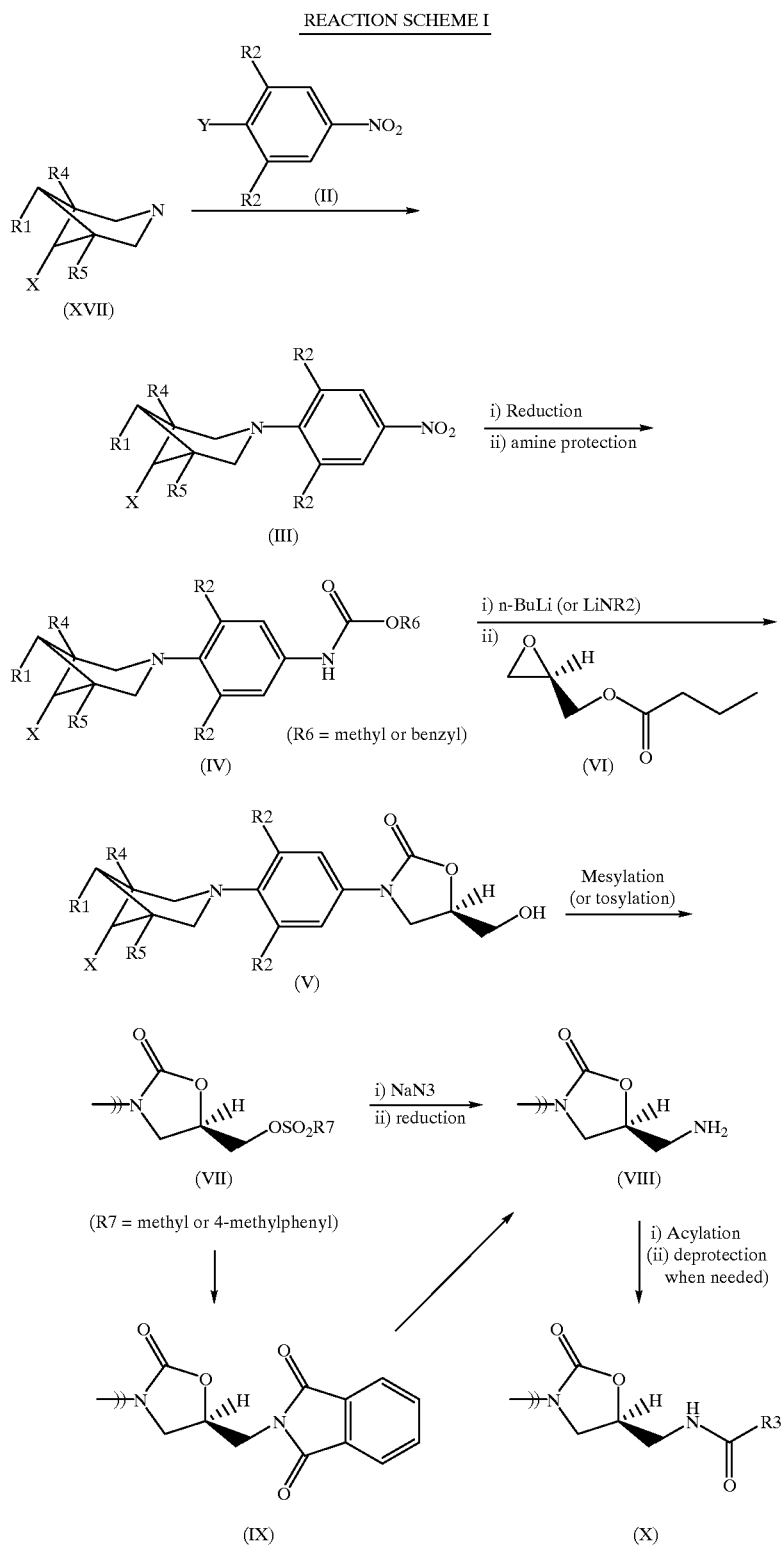

REACTION SCHEME II

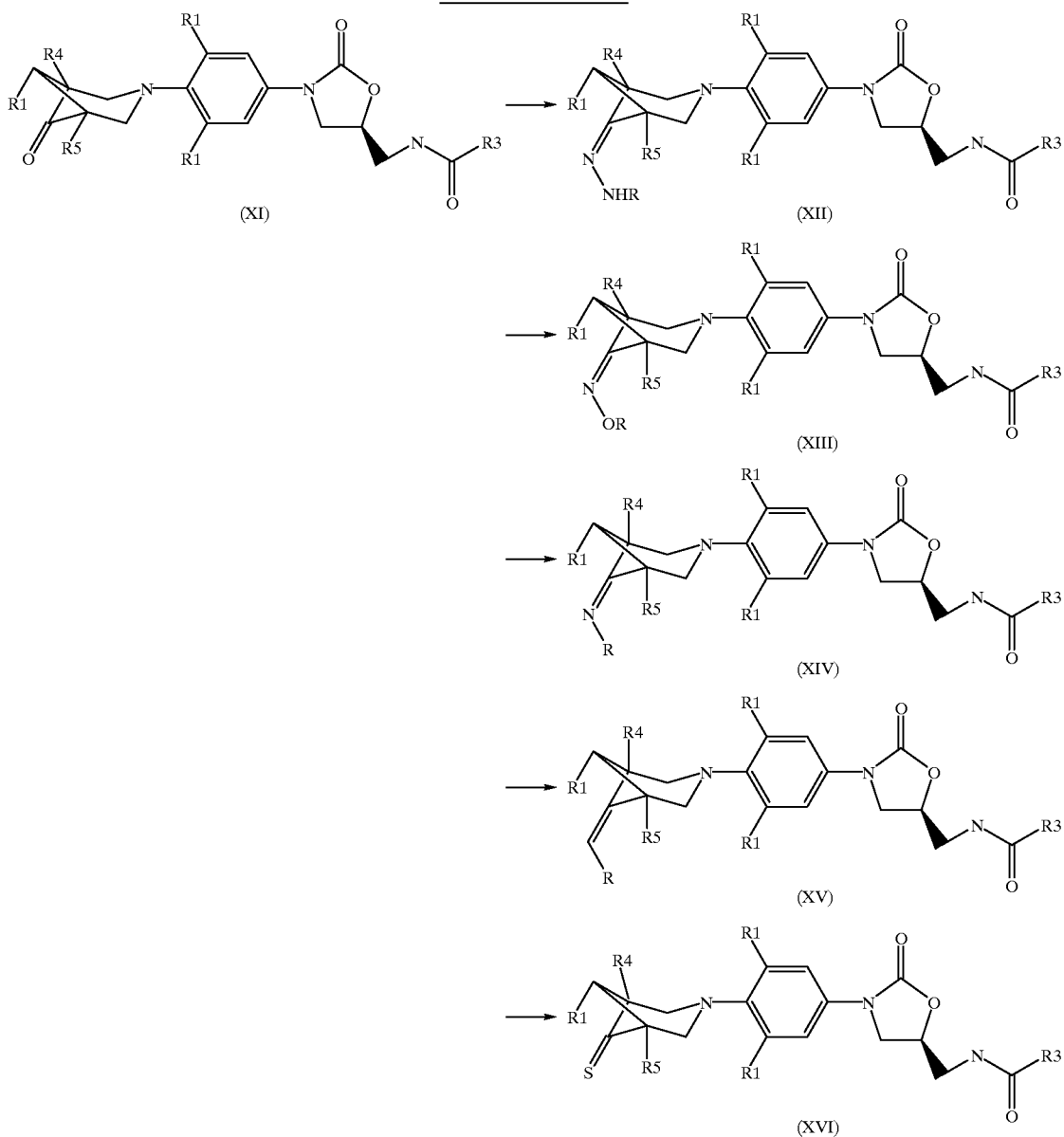

As shown in Reaction Scheme I, 3-azabicyclo[3.1.1] heptane heterocyclic amine derivatives XVII are reacted with a functionalized nitrobenzene II in the presence of a suitable base and in a suitable solvent to provide the compounds III. The functionalization of the nitrobenzene II is for the purpose of inducing the aromatically nucleophillic reaction. For examples, the reaction can be carried out in dimethylsulfoxide in the presence of dibasic potassium phosphate, or in aprotic solvent such as acetonitrile, tetrahydrofuran or chloroform in the presence of organic base such as N,N-diisopropylethylamine or triethylamine to yield the compounds III. The preferred temperature for the reaction will range from room temperature to 80° C.

The X, R1, R4 and R5 substituents may be protected by suitable protecting groups to prevent the said substituents from participating in the undesired reaction so that no side reaction products may be formed. For example, if X is carbonyl, then it can be protected by a ketal, so that it will prevent the X group from reacting with the primary amine to be formed afterward. The reactions involving the protection and deprotection of the functional groups are conventional techniques and, for example, can be carried out as described in Greene, T. W., etc. "Protective Group in Organic Synthesis" 2nd edition and John Wiley & Sons: New York, 1991.

The nitro group of the compound III is then reduced by catalytic hydrogenation in the presence of a suitable catalyst such as 5% to 10% palladium on carbon or W-2 Raney nickel and in a suitable solvent such as tetrahydrofuran/water to provide the amine derivatives. In addition, there can be a number of conventional methods to accomplish the reduction. Following the removal of the residual catalysts and, if desired, the concentration of the solution, the formed amine derivatives is directly reacted with suitable base and alkyl or aryl chloroformate without purification to provide the urethane derivatives IV. Fox example, the reaction can be carried out by using sodium bicarbonate and benzyl or methyl chloroformate. The urethanes IV are then deprotonated with a suitable base such as n-butyllithium, lithium diisopropylamide or lithium bis(trimethylsilyl)amide in a suitable solvent such as tetrahydrofuran or ether and at a suitable temperature such as −78° C. to −60° C. to give a lithiated intermediate which is then treated with commercially available (R)-(-)-glycidyl butyrate. After the reaction solution is warmed, water and water insoluble organic solvent such as chloroform and ethylacetate were added to the solution, thereby obatining pure enantiomer of 5-(hydroxymethyl)oxazolidinone.

The compound V is then converted to the corresponding mesylate or aryl sulfonate (for example, p-toluenesulfonyl) by the action of, for example, methanesulfonyl chloride/pyridine or methanesulfonyl chloride/triethylamine/dichloromethane or p-tolunesulfonyl chloride/pyridine.

The sulfonate derivative is then reacted with an azide source such as sodium or potassium azide in an aprotic solvent such as N,N-dimethylformamide or 1-methyl-2-pyrrolidinone at 50 to 90° C. to provide the intermediate azide. The rate of the reaction will be increased by using a catalyst such as 18-crown-6.

The azide is then reduced by hydrogenation with palladium on carbon or platinum catalyst in an appropriate solvent such as ethyl acetate or methanol to form the corresponding amine VIII. Alternatively, the conversion of the azide into the amine can be accomplished by using a phosphorous compound such as triphenylphosphine in a suitable solvent such as water/tetrahydrofuran.

Alternatively, the conversion of the sulfonate derivatives VII into the amine VIII can be accomplished via the intermediate phthalimide. For example, the sulfonate derivatives are reacted with potassium phthalimide in acetonitrile at reflux temperature to form the intermediate phthalimide IX which is then deprotected to afford the amine VIII.

In yet another alternative, the mesylate VII can be directly converted into the amine VIII in a suitable solvent such as water/isopropanol/tetrahydrofuran.

The resultant amine VIII is then acylated by conventional methods, for example, by reacting with an acid chloride or anhydride in a basic solvent such as pyridine at a temperature of −50° C. to 50° C. to yield the acylated compound X.

As shown in Reaction Scheme II, the compound X, themselves examples of antibacterial oxazolidinone of the general formula I according to the present invention, can be further elaborated to additional compounds of the general formula I. Specifically, the carbonyl derivative XI (X=carbonyl) can be reacted with hydrazine by a conventional method to afford the corresponding hydrazine derivative XII. The compound XI can be reacted with hydroxylamine hydrochloride or methoxylamine hydrochloride in a suitable solvent such as pyridine according to a conventional method to provide the corresponding oxime derivatives XIII. The compound XI can be reacted with primary amine to obtain the corresponding imine derivatives XIV. The compound XI can be converted into the corresponding olefin derivatives XV through Wittig reaction by treatment with phosphorus ylide according to a conventional method. The compound XI can be converted into the corresponding thioketone XVI by treatment with Lawesson's reagent according to a conventional method.

The above procedures and reaction conditions can be referenced in Greene, T. W. "Protective Groups in Organic Synthesis", 2nd edition; John Wiley & Sons: New York, 1991; Francis A. Carey "Advanced Organic Chemistry" 3rd edition; Plenum Press, March J. "Advanced Organic Chemistry" 4th edition; John Wiley & sons: New York, 1992.

The present compounds are active against a number of known antibiotics-resistant human and veterinary pathogens, including Gram-positive aerobic bacteria such as Staphylococci, Streptococci and Enterococci as well as anaerobic microorganisms such as Clostridia sp., and acid-fast microorganisms such as Micobacterium sp., for example *Mycobacterium tuberculosis, Mycobacterium avium.*

In another aspect, the present invention provides an antibacterial composition comprising the compound of the general formula I of the present invention as an active ingredient.

The antibacterial composition of the present invention may be prepared by containing only the compound of the general formula I of the present invention per se or by combining the compound of the general formula I of the present invention with a solid or liquid pharmaceutically acceptable carrier and, optionally, with pharmaceutically acceptable adjuvants and excipients using standard and conventional techniques. The antibacterial composition may be formulated into a liquid, solid or semi-solid form to be orally, parenterally or locally administered. Such formulations include tablets, solutions, capsules, granules, powders, syrups, injections, cachets, suppositories, ointments, etc.

The antibacterial composition of the present invention may be directly used to human or animals and also applied as agricultural medicines or food preservatives. In therapeutic use for treating or combating bacterial infections in human or animals, the antibacterial composition of the present invention is preferably administered by oral route or injection. Such dosages may vary depending on the age or weight of the patient, the severity of the bacterial infection being treated, the administration route, etc. Generally, the amount of the activie component is in the range of 1 to 1,000 mg/kg of body weight/day, preferably 10 to 500 mg/kg of body weight/day. The daily dosage according to the present invention may be administered once or in mutiple.

A carrier used in the solid formulation according to the present invention can be at least one substance which may also function as expander, flavoring agent, solubilizer, lubricant, suspending agent, binder, disintegrating agent and encapsulating agent. Inert solid carriers include magnesium carbonate, magnesium stearate, talc, sugar, lactose, pectin, dextrin, starch, gelatin, low melting wax, cocoa butter, and the like.

As a carrier used in the liquid formulation such as solution, suspension and emulsion, water, water-propylene glycol system or water-polyethylene glycol system, and optionally pigments, sweetners, flavoring agents, stabilizers and thickening agents may be used.

The pharmaceutical solutions for parenteral administration containing the compounds of formula I according to the present invention can be administered by intravenous injection, intramuscular injection or conventional injection manners. Such solutions for injection can contain the compounds of formula I per se or as a water soluble salt such as acid addition salt or base salt. The carrier for injection includes a pharmaceutically acceptable water, physiological saline and a buffer to provide a suitably buffered isotonic solution having a pH of about 3 to 7. Suitable buffering agents include, for example, trisodium orthophosphate, sodium bicarbonate, sodium citrate, N-methylglucamine, L-(+)-lysine, L-(+)-arginine and pharmaceutically widely employed buffering agents.

The invention will now be described with reference to the following illustrative Examples.

EXAMPLES

Reference Example 1

7-Exo-methylspiro[3-(para-toluenesulfonyl)-3-azabicyclo[3.1.1]heptan-6,2'-perhydro[1.3]dioxolane

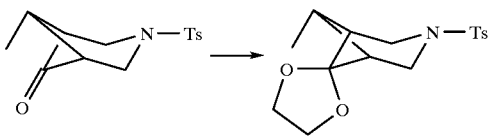

A solution of 13.3 g of known compound 7-exo-methyl-6-oxo-3-(para-toluenesulfonyl)-3-azabicyclo[3.1.1]heptane (Heterocycles, 1989, 25, p 29), 3.54 g of ethyleneglycol and 0.2 g of p-toluenesulfonic acid monohydrate in 250 ml of benzene was heated under reflux for 24 hours while removing water with a Dean Stark apparatus. After completion of the reaction, 200 ml of ethylacetate and 200 ml of saturated aqueous sodium carbonate solution were added to the reaction solution. The organic layer was separated from the aqueous layer and dried over anhydrous sodium sulfate, filtered and concentrated to obtain 15 g of the title compound.

400 MHz-$^1$H-NMR (CDCl$_3$)

7.7(2H,d), 7.3(2H,d), 3.6~4.0(4H,m), 3.6~3.8(4H,m), 2.5 (3H,s), 2.1(2H,s), 1.9(1H,m), 1.3(3H,d, J=7.1 Hz)

Reference Example 2

7-Exo-methylspiro[3-azabicyclo[3.1.1heptan-6,2'-perhydro[1.3]dioxolane

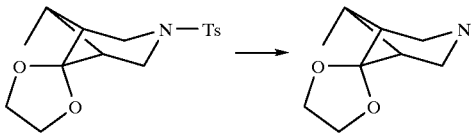

A solution of 8 g of the compound of REFERENCE EXAMPLE 1 in 60 ml of n-amylalcohol was heated under reflux for 3 hours while adding 10 g of sodium pieces. The reaction solution was cooled to 5° C. and 100 ml of water was slowly added to the solution. 100 ml of ethylacetate was added to separate the organic layer from the aqueous layer. The separated organic layer was dried over anhydrous sodium sulfate, filtered and concentrated under reduced pressure to obtain 4 g of the title compound.

400 MHz-$^1$H-NMR (CDCl$_3$)

3.8~4.0(4H,m), 3.1~3.4(4H,m), 2.3(1H,m), 2.1(2H,s) 2.0 (1H,m), 1.3(3H,d, J=7.1 Hz)

Reference Example 3

7-Exo-methylspiro[3-(2-fluoro-4-nitrophenyl)-3-azabicyclo[3.1.1]heptan-6,2'-perhydro[1.3]dioxolane

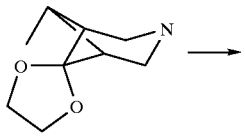

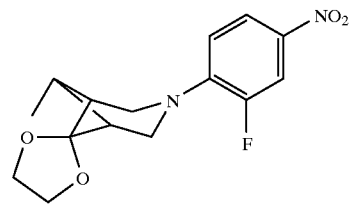

7.1 g of N,N-diisopropylethylamine was added to a solution of 9.2 g of the compound of REFERENCE EXAMPLE 2 in 150 ml of 1,2-dichloroethane. The reaction solution was cooled to 5° C. and 8.7 g of 3,4-difluoronitrobenzene was slowly added to the solution. After the reaction solution was heated under reflux for 24 hours, the solution was stood until the temperature was slowly lowered to 25° C. and concentrated under reduced pressure. After 50 ml of methanol was added to the concentrated residue, the resulting solution was cooled to 5° C. The yellow solid formed therefrom was filtered and dried to obtain 5 g of the title compound.

400 MHz-$^1$H-NMR (CDCl$_3$)

7.8~8.0(2H,m), 6.7(1H,m), 3.8~4.0(4H,m), 3.8~4.0(4H,m) 2.3(2H,s) 2.0(1H,m), 1.4(3H,d, J=7.1 Hz)

Reference Example 4

N-carboxybenzoxy-3-fluoro-4-(7-exo-methylspiro-[3-azabicyclo[3.1.1]heptan-6,2'-perhydro[1.3]dioxolane]-3-yl) aniline

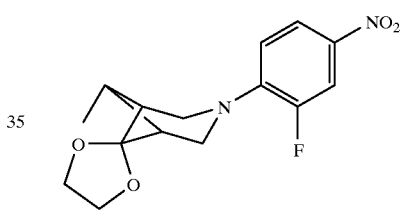

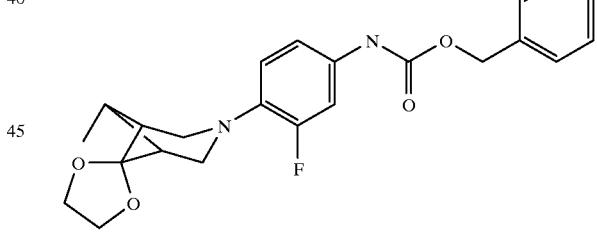

After 3.8 g of ammonium formate and 0.2 g of 10% palladium on carbon were added to a solution of 4.6 g of the compound of REFERENCE EXAMPLE 3 in a mixture of 80 ml of tetrahydrofuran and 80 ml of methanol, the reaction solution was heated under reflux for 3 hours. The solution was then cooled to 25° C. and filtered. The liquid filtrate was concentrated under reduced pressure. After the resultant residue was dissolved in 100 ml of acetone, 100 ml of aqueous solution of 3.8 g of sodium bicarbonate was added to the solution. After the reaction solution was cooled to 5° C., 3.2 ml of benzylchloroformate was slowly added to the solution, and stirred at 25° C. for 24 hours. After completion of the reaction, 200 ml of ethylacetate was added to extract the organic layer which was then washed with brine and dried over anhydrous sodium sulfate. Thereafter, filtration and concentration under reduced pressure afforded 7 g of the title compound.

400 MHz-¹H-NMR (CDCl₃)

7.3~7.4(5H,m), 7.2(1H,m), 6.9(1H,m), 6.7(1H,m), 6.5(1H,m), 5.2(2H,s), 3.7~4.0(8H,m), 2.3(2H,s), 2.2(1H,m), 1.4(3H,d, J=7.1 Hz)

Reference Example 5

(R)-[N-3-[3-fluoro-4-(7-exo-methylspiro-[3-azabicyclo[3.1.1]heptan-6,2'-perhydro[1.3]dioxolane]-3-yl)phenyl]-2-oxo-5-oxazolinyl]methanol

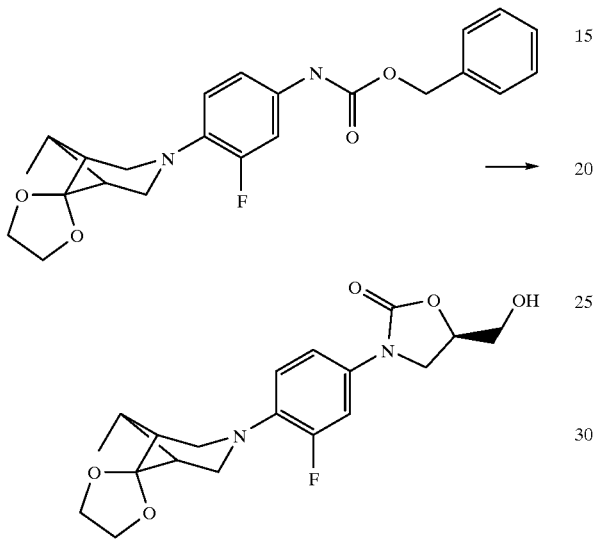

After 7 g of the compound of REFERENCE EXAMPLE 4 was dissolved in 200 ml of anhydrous tetrahydrofuran, the reaction solution was cooled to −78° C. under N₂ atmosphere. 11 ml of 2.5 M n-butyllitium was slowly added to the solution and reacted at the same temperature for 1.5 hours. 2.88 ml of R-(-)-glycidyl butyrate was slowly added dropwise to the reaction solution and reacted at the same temperature for 2 hours. The reaction solution was stood for 24 hours until the temperature was slowly warmed to 25° C. After completion of the reaction, the solution was cooled to 5° C. and 50 ml of saturated aqueous ammonium chloride solution was slowly added to the solution. Then, 200 ml of ethylacetate and then 20 ml of water were added. After the organic layer was separated from the aqueous layer, the organic layer was dried over anhydrous sodium sulfate, filtered and concentrated under reduced pressure. The concentrated residue was chromatographed over silica gel, eluting with ethylacetate/methanol (7:1) to obtain 4 g of the title compound.

400 MHz-¹H-NMR (CDCl₃)

7.2(1H,m), 7.0(1H,m), 6.7(1H,m), 4.7(1H,m), 3.7~4.0(12H,m), 2.2(2H,s), 2.1(1H,m), 1.4(3H,d,J=7.1 Hz)

Reference Example 6

(R)-[N-3-[3-fluoro-4-(7-exo-methylspiro-[3-azabicyclo[3.1.1]heptan-6,2'-perhydro[1.3]dioxolane]-3-yl)phenyl]-2-oxo-5-oxazolinyl]methyl methanesulfonate

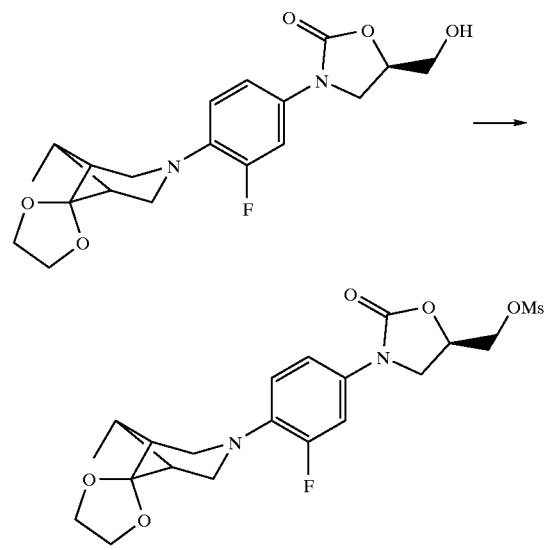

After 4 g of the compound of REFERENCE EXAMPLE 5 was dissolved in 50 ml of dichloromethane, 3.25 ml of triethylamine was added to the solution. The reaction solution was cooled to 5° C., and 1 ml of methansulfonyl chloride was slowly added to the solution and reacted at 25° C. for 24 hours. The completion of the reaction was affirmed by TLC analysis (ethylacetate Rf=0.6). 50 ml of water and 50 ml of dichloromethane were added to the solution. After the organic layer was separated from the aqueous layer, the organic layer was washed with brine and dried over anhydrous sodium sulfate. Filtration and concentration under reduced pressure afford 5 g of the title compound.

400 MHz-¹H-NMR (CDCl₃)

7.3(1H,m), 7.0(1H,m), 6.7(1H,m), 4.9(1H,m), 4.4(2H,m), 3.6~4.1(10H,m), 3.1(3H,s), 2.2(2H,s), 2.1(1H,m), 1.4(3H,d, J=7.1 Hz)

Reference Example 7

(R)-[N-3-[3-fluoro-4-(7-exo-methylspiro-[3-azabicyclo[3.1.1]heptan-6,2'-perhydro[1.3]dioxolane]-3-yl)phenyl]-2-oxo-5-oxazolinyl]methyl azide

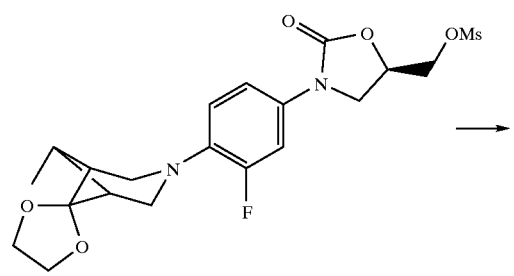

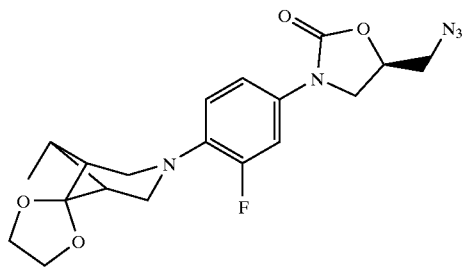

After 3.2 g of sodium azide was added to a solution of 5.2 g of the compound of REFERENCE EXAMPLE 6 in 30 ml of N,N-dimethylformamide, the reaction solution was heated to 75° C. for 24 hours. After completion of the reaction, the solution was cooled to 25° C. The solution was treated with 200 ml of ethylacetate and 100 ml of water to separate the organic layer. The separated organic layer was washed with 100 ml of water and then with brine, dried over anhydrous sodium sulfate, filtered and concentrated under reduced pressure to obtain 3.5 g of the title compound.

400 MHz-$^1$H-NMR (CDCl$_3$)

7.3(1H,m), 7.1(1H,m), 6.8(1H,m), 4.8(1H,m), 3.6~4.1 (12H,m), 2.2(2H,s), 2.1(1H,m), 1.4(3H,d,J=7.1 Hz)

Example 1

(S)-[N-3-[3-fluoro-4-(7-exo-methylspiro-[3-azabicyclo[3.1.1]heptan-6,2'-perhydro[1.3]dioxolane]-3-yl)phenyl]-2-oxo-5-oxazolidinyl]methyl]acetamide

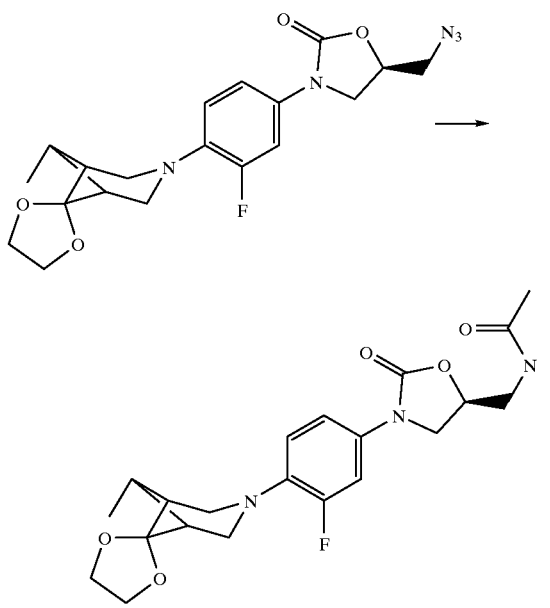

After 0.7 g of 10% palladium on carbon was added to a solution of 3 g of the compound of REFERENCE EXAMPLE 7 in 50 ml of ethylacetate, the hydrogenation was carried out at a hydrogen pressure of 50 psi. The completion of the reaction was affirmed by TLC analysis (chloroform:methanol=2:1 Rf=0.3). If TLC revealed the reaction to be incomplete, a further catalytic amount of 10% palladium on carbon was added to the reaction solution. After completion of the reaction, the solution was filtered and 1.3 g of pyridine was added to the liquid filtrate. The reaction solution was cooled to 5° C., and 3.0 g of acetic anhydride was added to the solution and reacted at 25° C. for 24 hours. After completion of the reaction was affirmed by TLC analysis (ethylacetate:ethanol=7:1 Rf=0.3), 20 ml of water and 50 ml of ethylacetate were added to separate the organic layer. The separated organic layer was washed with water followed by brine, dried over anhydrous sodium sulfate, filtered and concentrated under reduced pressure. The residue was treated with ethyl ether and n-hexane to obtain 3.5 g of the title compound as a white solid with mp 170° C.

400 MHz-$^1$H-NMR (CDCl$_3$)

7.3(1H,m), 7.0(1H,m), 6.7(1H,m), 6.2(1H,m), 4.7(1H,m), 3.6~4.0(12H,m), 2.2(2H,s), 2.1(1H,m), 2.0(3H,s), 1.4(3H,d, J=7.1 Hz)

Example 2

(S)-[N-3-[3-fluoro-4-(7-exo-methyl-6-oxo-3-azabicyclo[3.1.1]heptan-3-yl)phenyl]-2-oxo-5-oxazolidinyl]methyl]acetamide

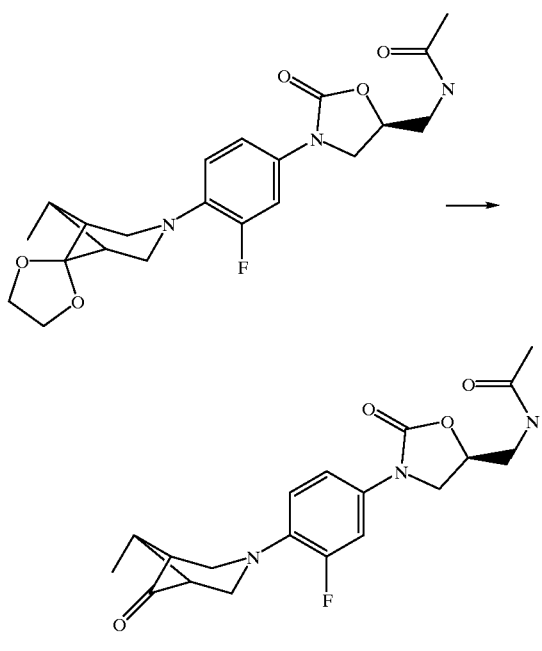

After 1 g of p-toluenesulfonic acid monohydrate was added to a solution of 1.4 g of the compound of EXAMPLE 1 in 60 ml of acetone and 4 ml of water, the reaction solution was heated under reflux for 7 hours. After completion of the reaction, 100 ml of ethyl acetate and 50 ml of saturated aqueous sodium carbonate solution was added to separate the organic layer. The separated organic layer was washed with 50 ml of chloroform. The extracted organic layer was dried over anhydrous sodium sulfate, filtered and concentrated under reduced pressure. The concentrated residue was chromatographed over silica gel, eluting with ethylacetate/methanol (5:1), to obtain 500 mg of the title compound with mp 152–155° C.

400 MHz-$^1$H-NMR (CDCl$_3$)

7.4(1H,m), 7.0(1H,m), 6.8(1H,m), 6.2(1H,m), 4.7(1H,m), 3.6~4.0(8H,m), 2.9(2H,s), 2.4(1H,m), 2.0(3H,s), 1.4(3H,d, J=7.1 Hz)

Example 3

(S)-[N-3-[3-fluoro-4-(7-exo-methyl-6-hydroxyimino-3-azabicyclo3.1.1]heptan-3-yl)phenyl]-2-oxo-5-oxazolidinyl]methyl]acetamide

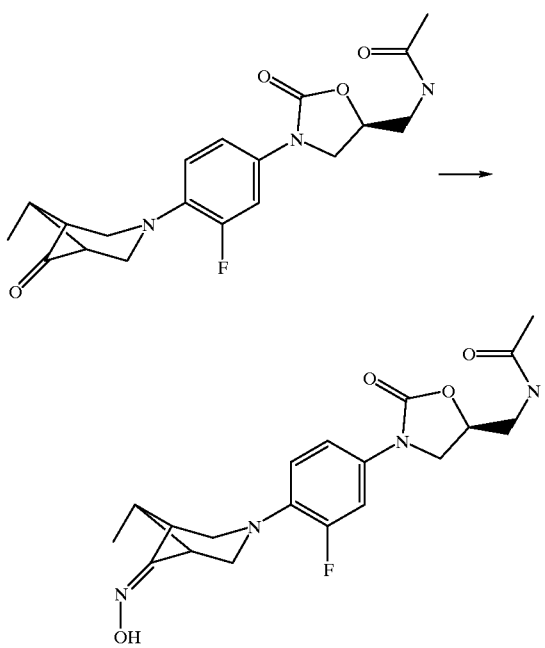

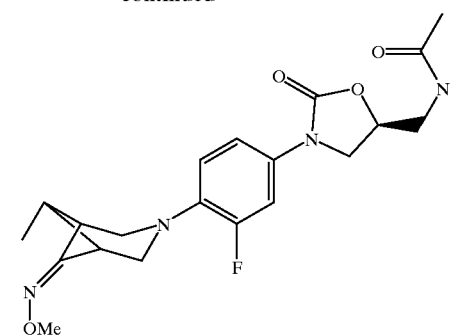

750 mg of sodium bicarbonate and 600 mg of hydroxyammonium chloride was added to a solution of 1.5 g of the compound of EXAMPLE 2 in 95% ethanol (5% water). The reaction solution was heated under reflux for 6 hours and concentrated. The concentrated residue was treated with 50 ml of chloroform and 30 ml of water to separate the organic layer. The separated organic layer was washed with 30 ml of aqueous 10% acetic acid solution and brine, dried over anhydrous sodium sulfate and concentrated under reduced pressure. The concentrated residue was treated with ethyl acetate and n-hexane, filtered and dried to obtain 700 mg of the title compound with mp 187–190° C.

400 MHz-$^1$H-NMR (CDCl$_3$)

7.4(1H,m), 7.0(1H,m), 6.7(1H,m), 6.2(1H,m), 4.7(1H,m), 3.6~4.0(8H,m), 2.8~3.3(2H,m), 2.2(1H,m), 2.0(3H,s), 1.4 (3H,d,J=7.1 Hz)

Example 4

(S)-[N-3-[3-fluoro-4-(7-exo-methyl-6-methoxyimino-3-azabicyclo[3.1.1]heptan-3-yl)phenyl]-2-oxo-5-oxazolidinyl]methyl]acetamide

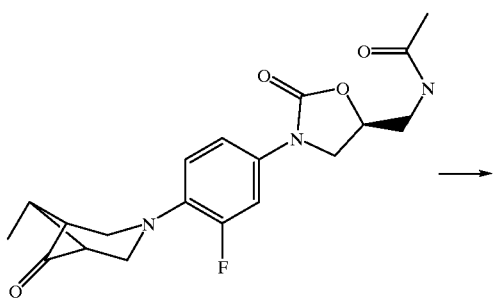

240 mg of methoxylamine hydrochloride was mixed with a solution of 900 mg of the compound of EXAMPLE 2 in 15 ml of pyridine at 25° C. for 24 hours. After completion of the reaction, the solution was concentrated under reduced pressure. The concentrated residue was treated with 50 ml of chloroform and 30 ml of water to separate the organic layer. The separated organic layer was dried over anhydrous sodium sulfate, filtered and concentrated under reduced pressure. The concentrated residue was chromatographed over silica gel, eluting with ethylacetate/methanol (7:1), to obtain 300 mg of the title compound with mp 160° C.

400 MHz-$^1$H-NMR (CDCl$_3$)

7.4(1H,m), 7.0(1H,m), 6.7(1H,m), 6.2(1H,m), 4.0(3H,s), 4.7(1H,m), 3.6~4.0(8H,m), 2.8~3.3(2H,m), 2.2(1H,m), 2.0 (3H,s), 1.2(3H,d)

Example 5

(S)-[N-3-[3-fluoro-4-(spiro[3-azabicyclo[3.1.1]heptan-6,2'-perhydro[1,3]dioxolane]3-yl)phenyl]-2-oxo-5-oxazolidinyl]methyl]acetamide

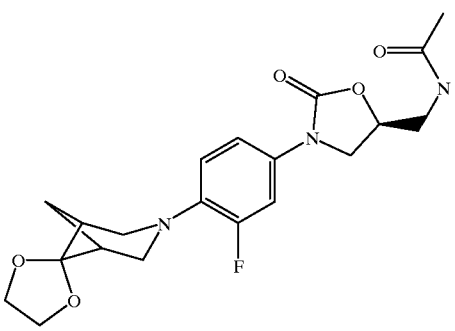

Following the procedures of REFERENCE EXMAPLES 1 to 7 and EXMAPLE 1, but using 10 g of known compound 6-oxo-3-(p-toluensulfonyl)-3-azabicyclo[3.1.1]heptan (Heterocycles, 1989, 25 p 29, 400 MHz-$^1$H-NMR(CDCl$_3$); 7.7(2H,d), 7.3(2H,d), 3.7~4.0(4H,m), 3.1(2H,m), 2.4(3H,s), 1.7~2.1(2H,m)) as a starting substance, 1.5 g of the title compound with mp 155–160° C. was obtained.

400 MHz-$^1$H-NMR (CDCl$_3$)

7.3(1H,m), 7.0(1H,m), 6.7(1H,m), 6.2(1H,m), 4.7(1H,m), 3.6~4.0(12H,m), 2.4(2H,m), 1.7~2.1(2H,m), 2.0(3H,s)

Example 6

(S)-[N-3-[3-fluoro-4-(6-oxo-3-azabicyclo[3.1.1]heptan-3-yl)phenyl]-2-oxo-5-oxazolidinyl]methyl]acetamide

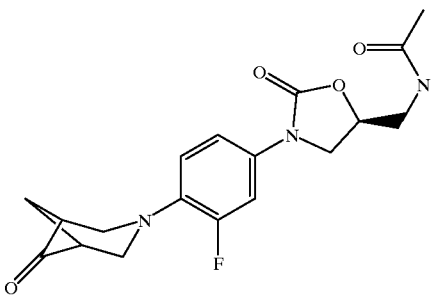

Following the procedure of EXAMPLE 2, but using 1.0 g of the compound of EXAMPLE 5, 200 mg of the title compound with mp 140–145° C. was obtained.

400 MHz-$^1$H-NMR (CDCl$_3$)
7.4(1H,m), 7.0(1H,m), 6.8(1H,m), 6.2(1H,m), 4.7(1H,m), 3.6~4.0(8H,m), 3.1(2H,m), 1.7~2.1(2H,m), 2.0(3H,s)

Example 7
(S)-[N-3-[3-fluoro-4-(6-hydroxyimino-3-azabicyclo[3.1.1]heptan-3-yl)phenyl]-2-oxo-5-oxazolidinyl]methyl]acetamide

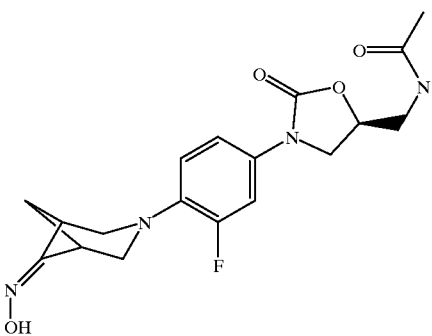

Following the precedure of EXAMPLE 3 but using 1.0 g of the compound of EXAMPLE 6, 300 mg of the title compound with mp 170° C. was obtained.

400 MHz-$^1$H-NMR (CDCl$_3$)
7.4(1H,m), 7.0(1H,m), 6.7(1H,m), 6.2(1H,m), 4.7(1H,m), 3.6~4.0(8H,m), 2.9~3.4(2H,m), 1.7~2.1(2H,m), 2.0(3H,s)

Example 8
(S)-[N-3-[3-fluoro-(6-methoxyimino-3-azabicyclo[3.1.1]heptan-3-yl)phenyl]2-oxo-5-oxazolidinyl]methyl]acetamide

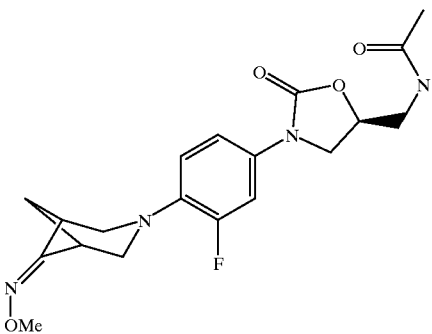

Following EXAMPLE 4 but using 1.0 g of the compound of EXAMPLE 6, 300 mg of the title compound with mp 160–165° C. was obtained.

400 MHz-$^1$H-NMR (CDCl$_3$)
7.4(1H,m), 7.0(1H,m), 6.7(1H,m), 6.2(1H,m), 4.7(1H,m), 4.0(3H,s), 3.6~4.0(8H,m), 2.9~3.4(2H,m), 1.7~2.1(2H,m), 2.0(3H,s)

Example 9
(S)-[N-3-[3-fluoro-4-(1-methyl-spiro[3-azabicyclo[3.1.1]heptan-6,2'-perhydro[1,3] dioxolane]-3-yl)-3-yl)phenyl]-2-oxo-5-oxazolidinyl]methyl]acetamide

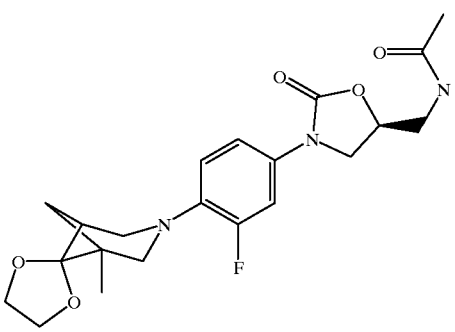

Following the procedures of REFERENCE EXAMPLES 1 to 7 and EXAMPLE 1, but using 10 g of known compound 1-methyl-6-oxo-3-(p-toluensulfonyl)-3-azabicyclo[3.1.1]heptane (Heterocycles, 1989, 25, p 29, 400 MHz-$^1$H-NMR (CDCl$_3$); 7.7(2H,d), 7.3(2H,d), 3.6~4.0(4H,m), 2.7(1H,m), 2.4(3H,s), 1.7~2.1(2H,m), 1.2(3H,s)) as a starting substance, 1.5 g of the title compound with mp 135–140° C. was obtained.

400 MHz-$^1$H-NMR (CDCl$_3$)
7.3(1H,m), 7.0(1H,m), 6.7(1H,m), 6.2(1H,m), 4.7(1H,m), 3.6~4.0(12H,m), 2.5(1H,m), 1.6~2.0(2H,m), 2.0(3H,s), 1.1 (3H,s)

Example 10
(S)-[N-3-[3-fluoro-4-(1-methyl-6-oxo-3-azabicyclo[3.1.1]heptan-3-yl)phenyl]-2-oxo-5-oxazolidinyl]methyl]acetamide

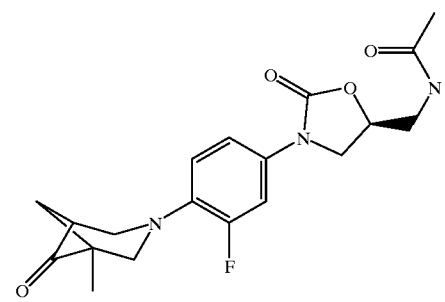

Following the procedure of EXAMPLE 2 but using 1.0 g of the compound of EXAMPLE 9, 200 mg of the title compound with mp 120–125° C. was obtained.

400 MHz-$^1$H-NMR (CDCl$_3$)
7.4(1H,m), 7.0(1H,m), 6.8(1H,m), 6.2(1H,m), 4.7(1H,m), 3.6~4.0(8H,m), 3.2(1H,m), 1.7~2.1(2H,m), 2.0(3H,s), 1.3 (3H,s)

Example 11
(S)-[N-3-[3-fluoro-4-(1-methyl-6-hydroxyimino-3-azabicyclo[3.1.1]heptan-3-yl)phenyl]-2-oxo-5-oxazolidinyl]methyl]acetamide

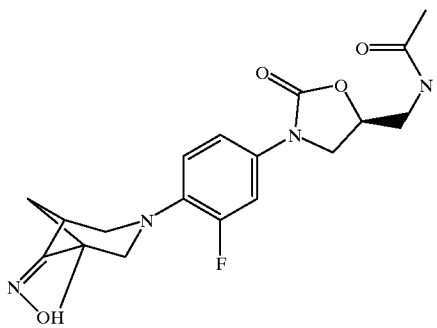

Following the procedure of EXAMPLE 3 but using 1.0 g of the compound of EXAMPLE 10, 300 mg of the title compound with mp 150° C. was obtained.

400 MHz-$^1$H-NMR (CDCl$_3$)

7.4(1H,m), 7.0(1H,m), 6.7(1H,m), 6.2(1H,m), 4.7(1H,m), 3.6~4.0(8H,m), 3.0~3.4(1H,m), 1.7~2.1(2H,m), 2.0(3H,s), 1.3(3H,s)

Example 12

(S)-[N-3-[3-fluoro-4-(1-methyl-6-methoxyimino-3-azabicyclo[3.1.1]heptan-3-yl)phenyl]-2-oxo-5-oxazolidinyl]methyl]acetamide

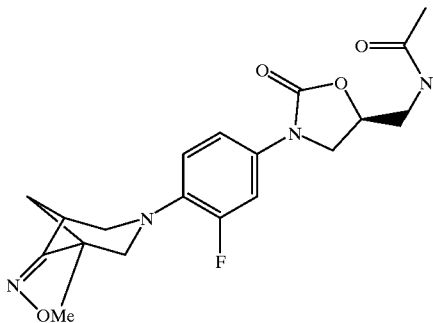

Following the procedure of EXAMPLE 4 but using 1.0 g of the compound of EXAMPLE 10, 300 mg of the title compound with mp 135–140° C. was obtained.

400 MHz-$^1$H-NMR (CDCl$_3$)

7.4(1H,m), 7.0(1H,m), 6.7(1H,m), 6.2(1H,m), 4.7(1H,m), 4.0(3H,s), 3.6~4.0(8H,m), 3.0~3.4(1H,m), 1.7~2.1(2H,m), 2.0(3H,s), 1.3(3H,s)

Experimental Example 1

Determination of In Vivo Antimicrobial Activity

A agar dilution test was carried out as described in Chemotheraphy, 29(1), 76, (1981) to determine the MIC (Minimum Inhibitory Concentration: mcg/ml) of each of compounds of EXAMPLES 1 to 12 against Gram-positive microorganisms or antibiotics-resistant microorganisms. The present compounds were compared against a well-known antibiotic vancomycin and U-100766 developed by Pharmacia & Upjohm as controls. The data is shown in Table 1.

TABLE 1

| Example No. | Microbes | | | | | |
|---|---|---|---|---|---|---|
| | A | B | C | D | E | F |
| 1 | 8.00 | 8.00 | 4.00 | 8.00 | 8.00 | 4.00 |
| 2 | 1.00 | 1.00 | 0.50 | 1.00 | 1.00 | 0.25 |
| 3 | 2.00 | 1.00 | 0.50 | 0.50 | 0.50 | 0.25 |
| 4 | 16.00 | 16.00 | 4.00 | 8.00 | 8.00 | 4.00 |
| 5 | 8.00 | 8.00 | 4.00 | 8.00 | 8.00 | 4.00 |
| 6 | 1.00 | 1.00 | 0.50 | 1.00 | 1.00 | 0.25 |
| 7 | 1.00 | 1.00 | 0.50 | 0.50 | 0.50 | 0.25 |
| 8 | 8.00 | 8.00 | 4.00 | 4.00 | 4.00 | 2.00 |
| 9 | 8.00 | 8.00 | 8.00 | 8.00 | 8.00 | 4.00 |
| 10 | 2.00 | 2.00 | 1.00 | 2.00 | 1.00 | 0.50 |
| 11 | 2.00 | 2.00 | 0.50 | 0.50 | 1.00 | 0.50 |
| 12 | 16.00 | 8.00 | 8.00 | 8.00 | 8.00 | 8.00 |
| Vancomycin | 1.00 | 1.00 | 1.00 | 4.00 | 2.00 | 0.50 |
| U-100766 | 2.00 | 1.00 | 0.50 | 2.00 | 2.00 | 1.00 |

A: *Staphylococcus aureus* ATCC 29213
B: MRSA C6068
C: *Staphylococcus epidermidis* ATCC 12228
D: *Enterococcus faecium* C 2252
E: *Enterococcus faecalis* ATCC 29212
F: *Streptococcus pyogenes* ATCC 8668

A: *Staphylococcus aureus* ATCC 29213
B: MRSA C6068
C: Staphylococcus epidermidisATCC 12228
D: Enterococcus faeciumC 2252
E: Enterococcus faecalisATCC 29212
F: Streptococcus pyogenesATCC 8668

From the data of the Table 1, it is evident that the compounds of the general formula I according to the present invention are remarkably effective antibacterial agents compared to the well-known antibiotic vancomycin.

What is claimed is:

1. A compound of formula 1:

Formula I

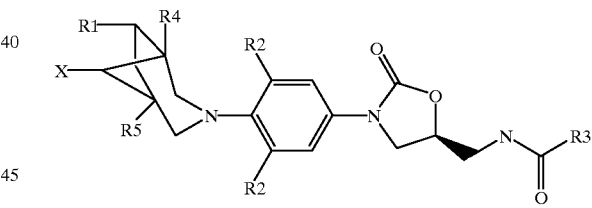

or a salt or hydrate thereof in which

R1, R4 and R5 are independently selected from the group consisting of (i) hydrogen, (ii) $C_1$–$C_6$ alkyl unsubstituted or substituted with at least one of F, Cl, hydroxy, $C_1$–$C_3$ alkyl, $C_1$–$C_6$ alkoxy and $C_1$–$C_6$ acyloxy and (iii) $C_3$–$C_6$ cycloalkyl;

R2 is independently H, F, Cl or methoxy;

R3 is selected from the group consisting of (i) hydrogen, (ii) $C_1$–$C_6$ alkyl unsubstituted or substituted with at least one of F, Cl, hydroxy, $C_1$–$C_3$ alkyl, $C_1$–$C_6$ alkoxy and $C_1$–$C_6$ acyloxy, (iii) $C_3$–$C_6$ cycloalkyl, (iv) amino, (v) $C_1$–$C_6$ alkylamino, (vi) $C_1$–$C_6$ dialkylamino and (vii) $C_1$–$C_6$ alkoxy; and X, together with the carbon to which X is attached, form (i) carbonyl, (ii) thiocarbonyl, (iii) ethyleneketal, propyleneketal, dimethylketal or diethylketal, (iv) oxime unsubstituted or substituted with $C_1$–$C_5$ alkyl which is optionally substituted with at least one of Cl, F, hydroxy, $C_1$–$C_3$ alkoxy and $C_1$–$C_6$ acyloxy, or $C_1-C_5$ acyl which is optionally substituted with at least one of Cl, F, hydroxy, $C_1-C_3$ alkoxy and $C_1-C_6$ acyloxy, (v) hydrazone unsubstituted or substituted with $C_1-C_5$ alkyl which is optionally substituted with at least one of Cl, F, hydroxy, $C_1-C_3$ alkoxy, $C_1-C_3$ acyloxy and phenyl, $C_1-C_5$ acyl which is optionally substituted with at least one of Cl, F, hydroxy, $C_1-C_3$ alkoxy, $C_1-C_3$ acyloxy and phenyl, $C_1-C_5$ alkoxycarbonyl which is optionally substituted with at least one of Cl, F, hydroxy, $C_1-C_3$ alkoxy, $C_1-C_3$ acyloxy and phenyl, or $C_1-C_5$ alkylsulfonyl (vi) imine unsubstituted or substituted with $C_1-C_5$ alkyl which is optionally substituted with at least one of Cl, F, hydroxy, $C_1-C_3$ alkoxy, $C_1-C_3$ acyloxy and phenyl, or $C_1-C_5$ acyl which is optionally substituted with at least one of Cl, F, hydroxy, $C_1-C_3$ alkoxy, $C_1-C_3$ acyloxy and phenyl, or (vii) carbon-carbon double bond unsubstituted or substituted with $C_1-C_4$ alkoxycarbonyl, or $C_1-C_4$ alkyl which is optionally substituted with Cl, F, hydroxy, $C_1-C_3$ alkoxy or phenyl.

2. The compound of claim 1 which is (S)-N-[[3-[3-fluoro-4-(7-exo-methylspiro-[3-azabicyclo[3.1.1]heptan-6,2'-perhydro[1,3]dioxolane]-3-yl)phenyl]-2-oxo-5-oxazolidinyl] methyl]acetamide.

3. The compound of claim 1 which is (S)-N-[[3-[3-fluoro-4-(7-exo-methyl-6-oxo-3-azabicyclo[3.1.1]heptan-3-yl)phenyl]-2-oxo-3-oxazolidinyl]methyl]acetamide.

4. The compound of claim 1 which is (S)-N-[[3-[3-fluoro-4-(7-exo-methyl-6-hydroxyimino-3-azabicyclo[3.1.1]heptan-3-yl)phenyl]-2-oxo-5-oxazolidinyl]methyl]acetamide.

5. The compound of claim 1 which is (S)-N-[[3-[3-fluoro-4-(7-exo-methyl-6-methoxyimino-3-azabicyclo[3.1.1]heptan-3-yl)phenyl]-2-oxo-5-oxazolidinyl]methyl]acetamide.

6. The compound of claim 1 which is (S)-N-[[3-[3-fluoro-4-(spiro[3-azabicyclo[3.1.1] heptan-6,2'-perhydro[1,3] dioxolane]-3-yl)phenyl]-2-oxo-5-oxazolidinyl]methyl]acetamide.

7. The compound of claim 1 which is (S)-N-[[3-[3-fluoro-4-(6-oxo-3-azabicyclo[3.1.1] heptan-3-yl)phenyl]-2-oxo-5-oxazolidinyl]methyl]acetamide.

8. The compound of claim 1 which is (S)-N-[[3-[3-fluoro-4-(6-hydroxyimino-3-azabicyclo[3.1.1]heptan-3-yl) phenyl]-2-oxo-5-oxazolidinyl]methyl]acetamide.

9. The compound of claim 1 which is (S)-N-[[3-[3-fluoro-4-(6-methoxyimino-3-azabicyclo[3.1.1]heptan-3-yl) phenyl]-2-oxo-5-oxazolidinyl]methyl]acetamide.

10. The compound of claim 1 which is (S)-N-[[3-[3-fluoro-4-(1-methyl-spiro[3-azabicyclo[3.1.1]heptan-6,2'-perhydro[1,3]dioxolane]-3-yl)phenyl]-2-oxo-5-oxazolidinyl]methyl] acetamide.

11. The compound of claim 1 which is (S)-N-[[3-[3-fluoro-4-(1-methyl-6-oxo-3-azabicyclo[3.1.1]heptan-3-yl) phenyl]-2-oxo-5-oxazolidinyl]methyl]acetamide.

12. The compound of claim 1 which is (S)-N-[[3-[3-fluoro-4-(1-methyl-6-hydroxyimino-3-azabicyclo[3.1.1] heptan-3-yl)phenyl]-2-oxo-5-oxazolidinyl]methyl] acetamide.

13. The compound of claim 1 which is (S)-N-[[3-[3-fluoro-4-(1-methyl-6-methoxyimino-3-azabicyclo[3.1.1] heptan-3-yl)phenyl]-2-oxo-5-oxazolidinyl]methyl] acetamide.

14. The compound of claim 1 wherein one of R2 is F and another R2 is hydrogen.

15. The compound of claim 1 wherein each R2 is F.

16. The compound of claim 1 wherein R3 is hydrogen, methyl, difluoromethyl, dichloromethyl, hydroxymethyl or methoxy.

17. The compound of claim 1 wherein X, together with the carbon to which X is attached, form carbonyl.

18. The compound of claim 1 wherein X, together with the carbon to which X is attached, form oxime.

19. A process for producing a compound of formula I:

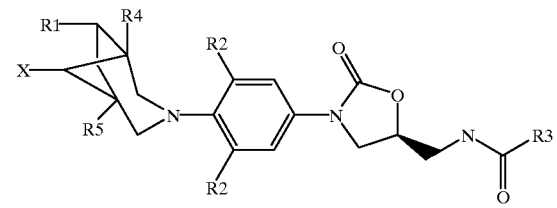

Formula I or a salt or hydrate thereof in which R1, R4 and R5 are independently selected from the group consisting of (i) hydrogen, (ii) $C_1-C_6$ alkyl unsubstituted or substituted with at least one of F, Cl, hydroxy, $C_1-C_3$ alkyl, $C_1-C_6$ alkoxy and $C_1-C_6$ acyloxy and (iii) $C_3-C_6$ cycloalkyl; R2 is independently H, F, Cl or methoxy; R3 is selected from the group consisting of (i) hydrogen, (ii) $C_1-C_6$ alkyl unsubstituted or substituted with at least one of F, Cl, hydroxy, $C_1-C_3$ alkyl, $C_1-C_6$ alkoxy and $C_1-C_6$ acyloxy, (iii) $C_3-C_6$ cycloalkyl, (iv) amino, (v) $C_1-C_6$ alkylamino, (vi) $C_1-C_6$ dialkylamino and (vii) $C_1-C_6$ alkoxy; and X, together with the carbon to which X is attached, form $C_1-C_5$ alkyl which is optionally substituted with at least one of Cl, F, hydroxy, $C_1-C_3$ alkoxy and $C_1-C_6$ acyloxy, or $C_1-C_5$ acyl which is optionally substituted with at least one of Cl, F, hydroxy, $C_1-C_3$ alkoxy and $C_1-C_6$ acyloxy, (v) hydrazone unsubstituted or substituted with $C_1-C_5$ alkyl which is optionally substituted with at least one of Cl, F, hydroxy, $C_1-C_3$ alkoxy, $C_1-C_3$ acyloxy and phenyl, $C_1-C_5$ acyl which is optionally substituted with at least one of Cl, F, hydroxy, $C_1-C_3$ alkoxy, $C_1-C_3$ acyloxy and phenyl, $C_1-C_5$ alkoxycarbonyl which is optionally substituted with at least one of Cl, F, hydroxy, $C_1-C_3$ alkoxy, $C_1-C_3$ acyloxy and phenyl, or $C_1-C_5$ alkylsulfonyl (vi) imine unsubstituted or substituted with $C_1-C_5$ alkyl which is optionally substituted with at least one of Cl, F, hydroxy, $C_1-C_3$ alkoxy, $C_1-C_3$ acyloxy and phenyl, or $C_1-C_5$ acyl which is optionally substituted with at least one of Cl, F, hydroxy, $C_1-C_3$ alkoxy, $C_1-C_3$ acyloxy and phenyl, or (vii) carbon-carbon double bond unsubstituted or substituted with $C_1-C_4$ alkoxycarbonyl, or $C_1-C_4$ alkyl which is optionally substituted with Cl, F, hydroxy, $C_1-C_3$ alkoxy or phenyl, which comprises reacting a compound of formula XVII:

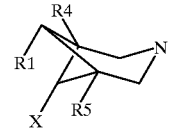

Formula XVII wherein R1, R4, R5 and X, together with the carbon to which X is attached, represent the same as defined above with a compound of formula II:

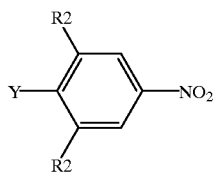

Formula II wherein R2 represents the same as defined above and Y is halogen or trifluoromethane sulfonate to provide a compound of formula III:

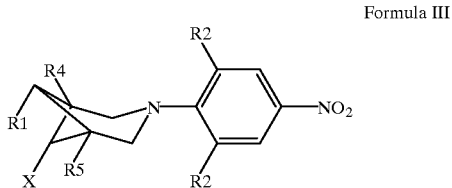

Formula III in which R1, R2, R4, R5 and X, together with the carbon to which X is attached, represent the same as defined above;

(b) reducing the compound of formula III to provide a compound of the formula IV:

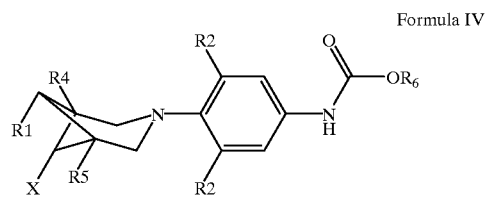

Formula IV in which R1, R2, R4, R5, and X, together with the carbon to which X is attached, represent the same as defined above and R6 is methyl or benzyl;

(c) reacting the compound of formula IV with (R)-(-)-glycidyl butyrate to provide a compound of formula V:

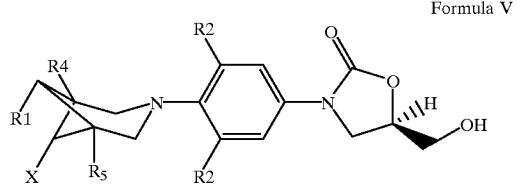

Formula V in which R1, R2, R4, R5 and X, together with the carbon to which X is attached, represent the same as defined above;

(d) inducing mesylation or tosylation of the compound of formula V to provide a compound of formula VII:

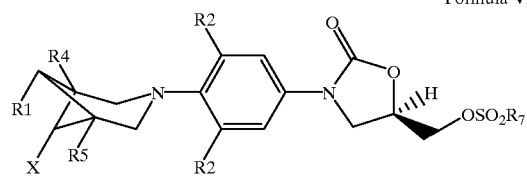

Formula VII in which R1, R2, R4, R5 and X, together with the carbon to which X is attached, represent the same as defined above and R7 is methyl or 4-methylphenyl; and (e) inducing amination of the compound of formula VII, followed by acylation to yield the compound of formula I.

20. The process of claim 19 which comprises further reacting the compound of formula XI:

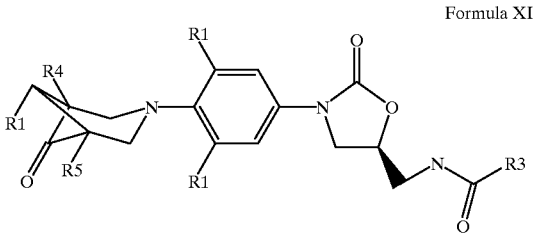

Formula XI in which R1, R3, R4 and R5 represent the same as defined in claim 19 with hydrazine to obtain the compound of formula XII:

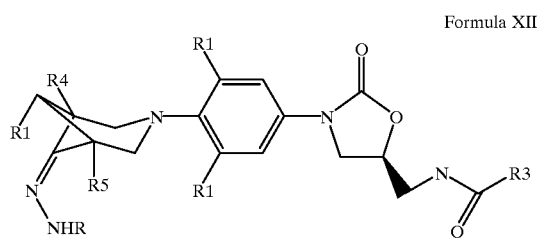

Formula XII in which R1, R3, R4 and R5 represent the same as defined in claim 19 and R is methyl or 4-methylphenyl.

21. The process of claim 19 which comprises further reacting the compound of formula XI:

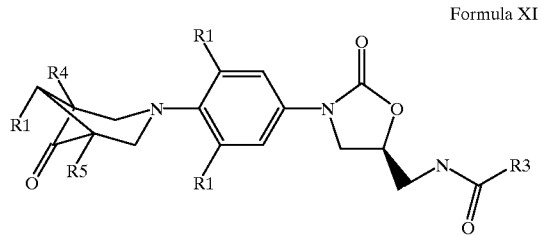

Formula XI in which R1, R3, R4 and R5 represent the same as defined in claim 19 with hydroxylamine hydrochloride or methoxylamine hydrochloride to obtain the oxime derivatives of formula XIII:

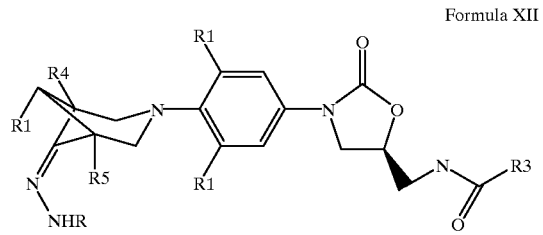

Formula XII in which R1, R3, R4 and R5 represent the same as defined in claim 19 and R is methyl or 4-methylphenyl.

22. The process of claim 19 which comprises further reacting the compound of the formula XI:

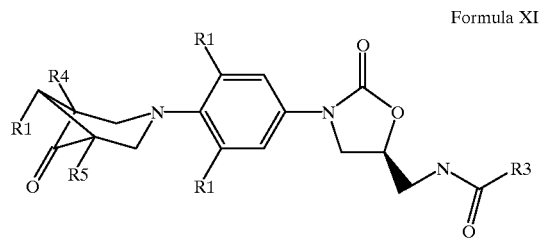

Formula XI in which R1, R3, R4 and R5 represent the same as defined in claim 19 with primary amine to obtain the imine derivatives of formula XIV:

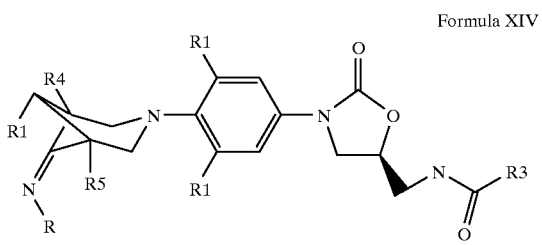

Formula XIV in which R1, R3, R4 and R5 represent the same as defined above and R is methyl or 4-methylphenyl.

23. The process of claim 19 which comprises further inducing Wittig reaction of the compound of formula XI:

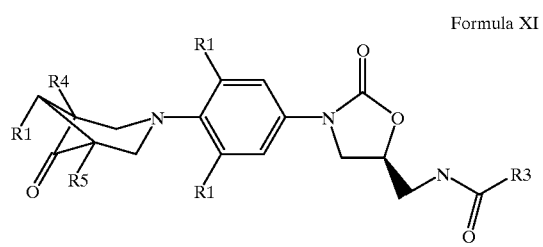

Formula XI in which R1, R3, R4 and R5 represent the same as defined in claim 19 to obtain the olefin derivatives of formula XV:

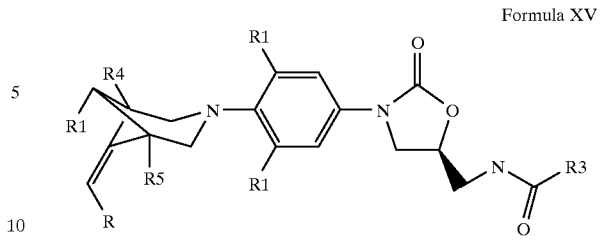

Formula XV in which R1, R3, R4 and R5 represent the same as defined in claim 19 and R is methyl or 4-methylphenyl.

24. The process of claim 19 which comprises further reacting the compound of formula XI:

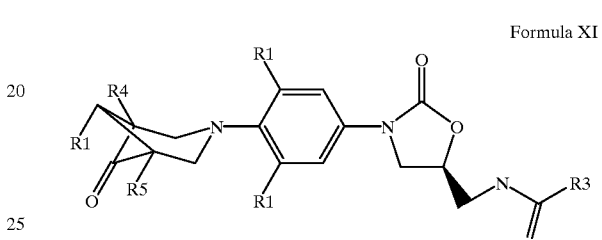

Formula XI in which R1, R3, R4 and R5 represent the same as defined in claim 19 with Lawesson's reagent to obtain the thioketone derivatives of formula XVI:

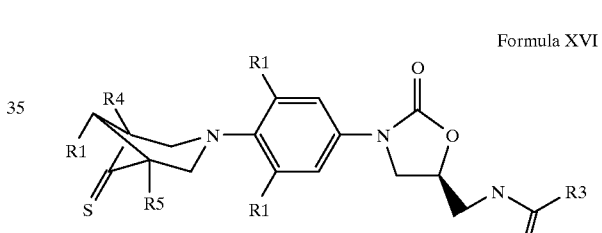

Formula XVI in which R1, R3, R4 and R5 represent the same as defined in claim 19 and R is methyl or 4-methylphenyl.

25. The process of claim 19 which comprises further conducting salt formation.

26. The process of claim 19 which comprises further conducting hydrate formation.

27. An antibacterial composition comprising an antibacterially effective amount of the compound according to claim 1 and a pharmaceutically acceptable carrier.

28. A method of treating a bacteria in a patient with an antibacterially effective compound comprising administering to the patient in need thereof an antibacterially effective amount of the compound of claim 1, optionally in combination with a pharmaceutically acceptable carrier.

* * * * *